US010895026B2

(12) United States Patent
Hamdani

(10) Patent No.: US 10,895,026 B2
(45) Date of Patent: Jan. 19, 2021

(54) SYSTEMS AND METHODS FOR MANUFACTURING A SOCK FOR MONITORING HEALTH CONDITIONS

(71) Applicant: Syed Talha Ali Hamdani, Faisalabad (PK)

(72) Inventor: Syed Talha Ali Hamdani, Faisalabad (PK)

(73) Assignee: National Textile University, Faisalabad, Faisalabad (PK)

(*) Notice: Subject to any disclaimer, the term of this patent is extended or adjusted under 35 U.S.C. 154(b) by 202 days.

(21) Appl. No.: 15/921,031

(22) Filed: Mar. 14, 2018

(65) Prior Publication Data
US 2019/0282165 A1    Sep. 19, 2019

(51) Int. Cl.
*D04B 1/26*      (2006.01)
*A61B 5/00*      (2006.01)
*A41B 11/00*     (2006.01)

(52) U.S. Cl.
CPC .............. *D04B 1/265* (2013.01); *A41B 11/00* (2013.01); *A61B 5/6807* (2013.01)

(58) Field of Classification Search
CPC . D04B 1/26; D04B 1/265; D04B 7/30; D04B 7/32; A61B 5/6807
See application file for complete search history.

(56) References Cited

U.S. PATENT DOCUMENTS

| | | | | |
|---|---|---|---|---|
| 6,941,775 | B2* | 9/2005 | Sharma | A41D 13/1281 2/902 |
| 8,476,172 | B2* | 7/2013 | Christof | D04B 1/16 442/2 |
| 2005/0034485 | A1* | 2/2005 | Klefstad-Sillonville | A41D 13/1281 66/171 |
| 2011/0015498 | A1* | 1/2011 | Mestrovic | A61B 5/01 600/301 |
| 2012/0144561 | A1* | 6/2012 | Begriche | D04B 1/22 2/243.1 |
| 2013/0137943 | A1* | 5/2013 | Pinto Rodrigues | A61B 5/01 600/301 |
| 2013/0192071 | A1* | 8/2013 | Esposito | A61B 5/1036 33/6 |

(Continued)

*Primary Examiner* — Danny Worrell
(74) *Attorney, Agent, or Firm* — Bajwa IP Law Firm; Haris Zaheer Bajwa

(57) ABSTRACT

A method for manufacturing a sock and monitoring health, comprising the steps of manufacturing the sock, comprising determining regions for conductive yarn patches in a sock, wherein the regions comprise of a heel region and a ball region, determining conductive part regions for a plurality of conductive paths connecting the respective heel region and the respective ball region to a top part of the sock, wherein at least two of the plurality of conductive paths are connected to the ball region and at least two of the plurality of conductive paths are connected to the heal region, and stitching the sock comprising stitching utilizing conductive yarn for the conductive yarn patches and the conductive paths, and stitching utilizing cotton yarn for the remaining of the socks. Furthermore, the method may include receiving signals from an end of the conductive part region responsive to receiving electrical signals from the heel region and the ball region, utilizing the received signals for determining health of a user.

2 Claims, 4 Drawing Sheets

402

404

(56) References Cited

U.S. PATENT DOCUMENTS

| | | | | |
|---|---|---|---|---|
| 2016/0186366 A1* | 6/2016 | McMaster | ................ | D04B 1/14 |
| | | | | 66/202 |
| 2016/0206242 A1* | 7/2016 | Esposito | .............. | A61B 5/1038 |
| 2016/0340811 A1* | 11/2016 | Roe | ...................... | A41B 11/005 |
| 2016/0367191 A1* | 12/2016 | Esposito | .............. | A61B 5/1038 |
| 2018/0249767 A1* | 9/2018 | Begriche | .............. | H05K 1/0283 |
| 2020/0008745 A1* | 1/2020 | Burch, V | .............. | A61B 5/7267 |

* cited by examiner

402

404

SYSTEMS AND METHODS FOR MANUFACTURING A SOCK FOR MONITORING HEALTH CONDITIONS

TECHNICAL FIELD

The present disclosure relates generally to a sock and a method for manufacturing a sock. More particularly, and without limitation, the present disclosure relates to structures and methods for manufacturing a sock structured so that it may be utilized to monitor health conditions.

BACKGROUND

Conventional socks with monitoring sensors have numerous drawbacks related to costs and performance. For example, the labor for applying sensors post productions to the socks is expensive as manufacturing these parts individually and then attaching them together may take a long time. Additionally, there is required a system to count an actual number of steps taken by a person in an accurate manner. Conventional procedures rely on utilizing GPS or general movement based technology to estimate steps. Accordingly, there is a need in the art for an exemplary system which may aid in counting each strike of a foot's heal/ball onto a surface, resulting in an accurate count of a number of steps.

SUMMARY

An object of the invention is to provide a new and improved sock for monitoring health data of a person.

In an exemplary embodiment, a method for manufacturing a sock and monitoring health, comprising the steps of manufacturing the sock, comprising determining regions for conductive yarn patches in a sock, wherein the regions comprise of a heel region and a ball region, determining conductive part regions for a plurality of conductive paths connecting the respective heel region and the respective ball region to a top part of the sock, wherein at least two of the plurality of conductive paths are connected to the ball region and at least two of the plurality of conductive paths are connected to the heal region, and stitching the sock comprising stitching utilizing conductive yarn for the conductive yarn patches and the conductive paths, and stitching utilizing cotton yarn for the remaining of the socks. Furthermore, the method may include receiving signals from an end of the conductive part region responsive to receiving electrical signals from the heel region and the ball region, utilizing the received signals for determining health of a user.

BRIEF DESCRIPTION OF THE DRAWINGS

The accompanying drawings, which are incorporated in and constitute a part of this specification, illustrate exemplary embodiments of the present disclosure and, together with the description, serve to explain the principles of the disclosure.

DETAILED DESCRIPTION

Embodiments consistent with the present disclosure enhance the performance and feel of a sock. Specifically, an exemplary method consistent with exemplary embodiments of which details are provide below and in the related figures, a sock is provided which aids in health monitoring of an individual. In exemplary embodiments, from the side of the medical practitioner, the continuous or ambulatory monitoring of health conditions is very important where the diagnosis is unclear or the abnormalities are happening infrequently. Being overweight is associated with the risk of numerous health problems such as diabetes, heart related problems, and various kind of cancers. Accordingly, it is imperative to have continuous monitoring of a patients, In exemplary embodiments, the exemplary sock and associated methods provide continuous and ubiquitous health monitoring. The exemplary socks integrate electromechanical material, such as piezo resistive fibers and/or yarns, creating structures that produce an electrical output in response to repetitive movements of human feet.

Accordingly, in an exemplary embodiment, a subject wearing socks may continuously monitor his/her health by being able to monitor information related to distance that they may have covered and/or a number of calories that may have been burnt during movement by, for example, walking or running. In exemplary embodiments, an exemplary distance may be calculated using information including an actual number of steps that a person may have. Furthermore, an exemplary overall system may include a pair of socks, a wireless system, and one or more processors. Accordingly, the pair of socks may serve as a sensor(s) and may transmit date related to information captured from exemplary socks wirelessly to an exemplary processor. Furthermore, data generated based on the transmitted data may be displayed on a user interface.

Figure 1:
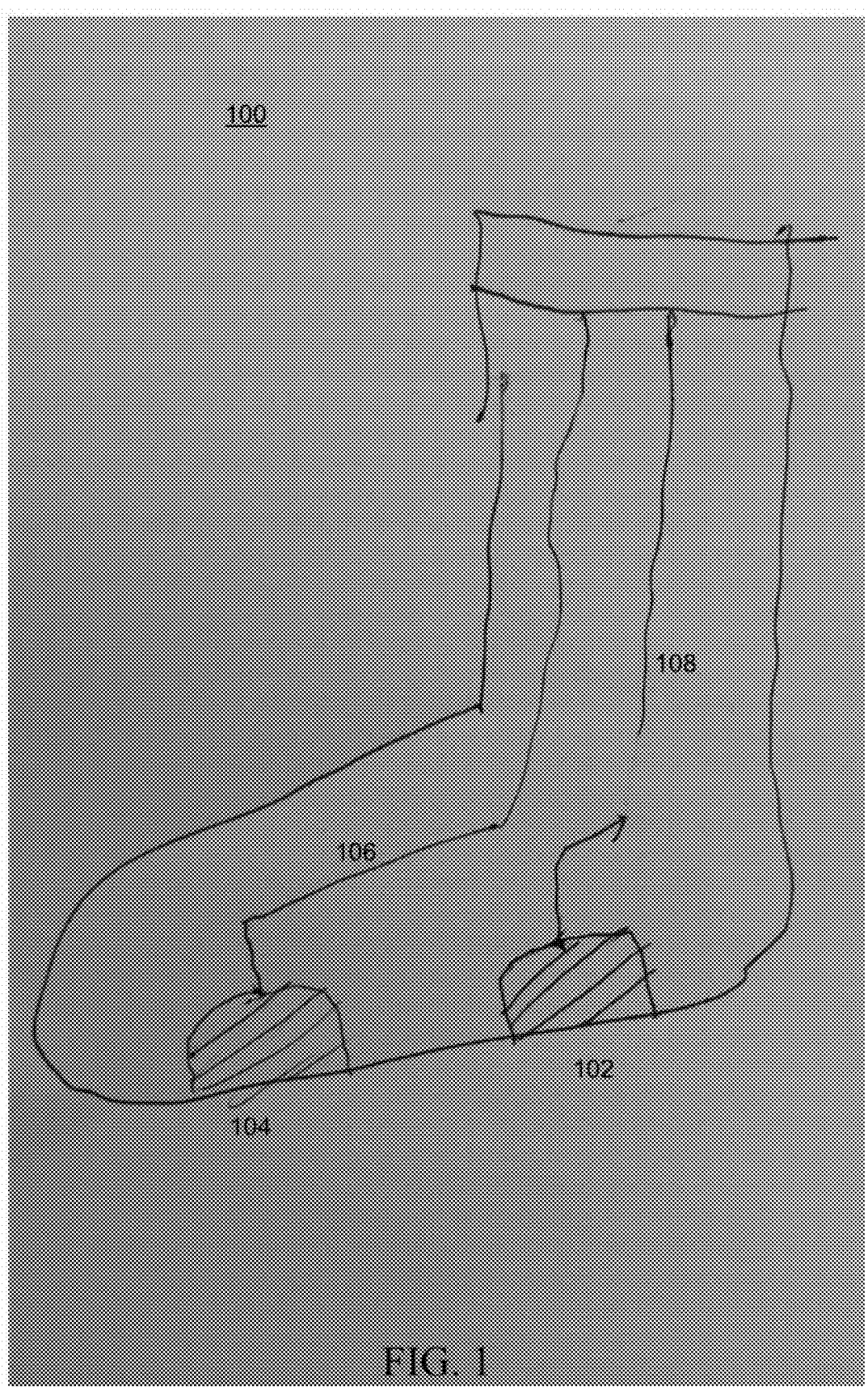
FIG. 1 illustrates and exemplary sock, consistent with one or more exemplary embodiments of the present disclosure

FIG. 1 illustrates and exemplary sock 100, consistent with one or more exemplary embodiments of the present disclosure. Sock 100 may comprise of a heel region 102, ball region 104, and respective conductive paths 106 and 108. In exemplary embodiments, there are conductive paths on the other side of the sock as well (not illustrated) similar to conductive paths 106 and 108. In exemplary embodiments, the heel region 102 and ball region 104 are designed to be positioned at a heel or ball of a person's foot. The exemplary heel region 102 and ball regions 104 are configured to be able to provide electrical signals to a monitoring through connected conductive paths based on a foot movement of a user.

Figure 2:
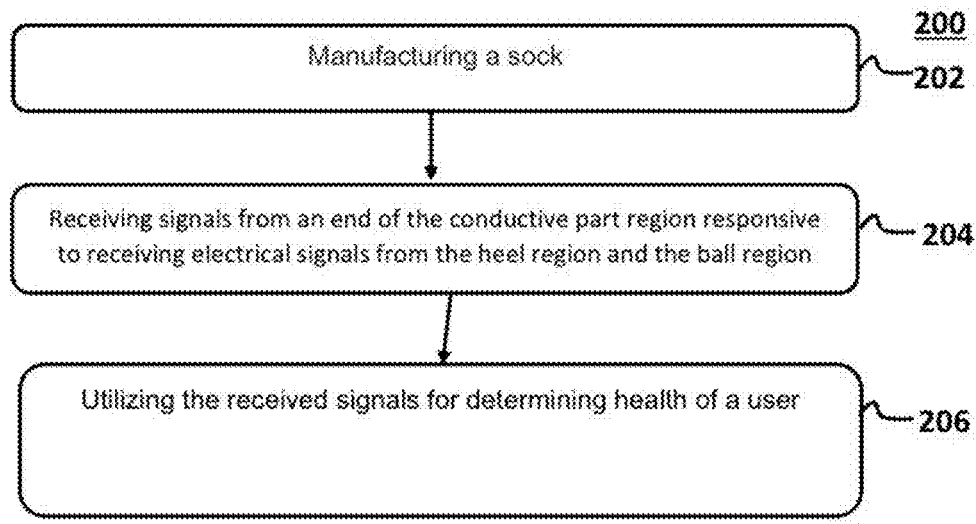
FIG. 2 illustrates an exemplary flowchart associated with a method for manufacturing a sock and monitoring health, consistent with one or more exemplary embodiments of the present disclosure.
Figure 3:
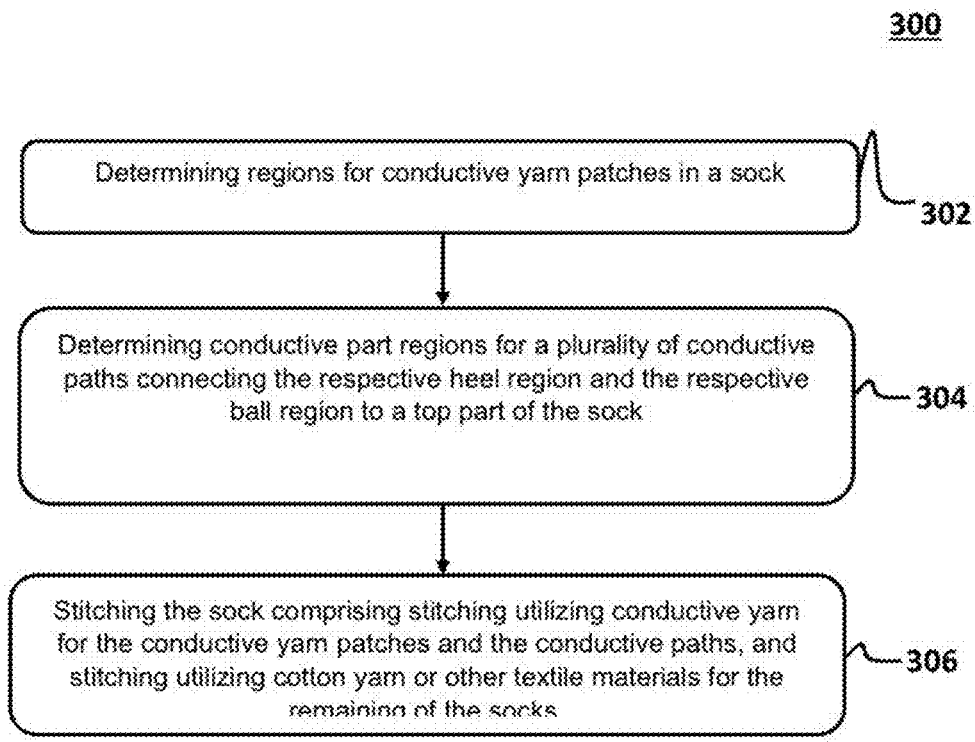
FIG. 3 illustrates an exemplary flowchart associated with a method for manufacturing a sock, consistent with one or more exemplary embodiments of the present disclosure.

FIG. 2 illustrates an exemplary method 200 for monitoring health of a person, consistent with one or more exemplary embodiments of the present disclosure. Step 202 may comprise manufacturing a sock. Exemplary details of step 202 are provided in the method 300 illustrated in FIG. 3. Step 302 may comprise of determining regions for conductive yarn patches in a sock. For example, the regions may comprise of heel region 102 and ball region 104. As described above, with respect to FIG. 1, the regions are designed to fall in line with a ball and heel region of a person's foot. In 0.0e2x emplary embodiments, the ball and heal regions may have area sizes of 5 cm by 4 cm and 5 cm by 3.5 cm. In additional embodiments, the sizes of the regions may be dependent on a size of a sock between a range of 4 cm by 3 cm to 6 cm by 4.5 cm, with the size of each dimension increasing respectively in a uniform manner in U.S. sizes 8 to 13.

Step 304 may comprise of determining conductive part regions for a plurality of conductive paths connecting the respective heel region and the respective ball region to a top part of the sock. In exemplary embodiments, at least two of the plurality of conductive paths are connected to the ball region and at least two of the plurality of conductive paths are connected to the hells region. The top ends of the conductive region may be connected to an exemplary processing unit.

Step 306 may comprise of stitching the sock comprising stitching utilizing conductive yarn for the conductive yarn patches and the conductive paths, and stitching utilizing cotton yarn or other textile materials for the remaining of the socks. In exemplary embodiments, only heel region 102, ball region 105, conductive paths 106 and 108, along with the unillustrated conductive paths are stitched using conductive yarn. The rest of sock 100 is stitched using cotton yarn or other textile materials. In exemplary embodiments, the rest of sock 100 may be stitched using additional materials instead of cotton yarn such as nylon, wool, acrylic, and polyester. In exemplary embodiments, elastane fiber may also used for socks manufacturing.

Figure 4:
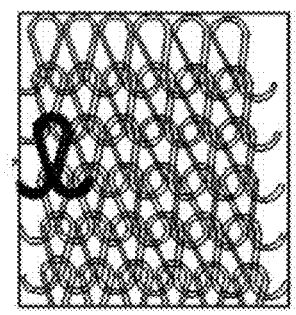
FIG. 4 illustrates stitch regions, consistent with one or more exemplary embodiments of the present disclosure.
Figure 4:
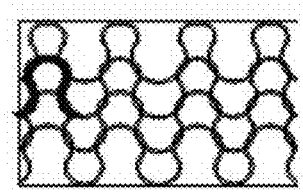

FIG. 4 illustrates stitch regions 402 and 404, consistent with one or more exemplary embodiments of the present disclosure. Stitch region 402 represents a region of the sock where cotton is utilized and stitch region 404 represents a region within the conductive path. As is illustrated in the stitch region 404, the respective stitch length is longer than the respective stitch length of stitches in stitch region 402. It is pertinent to note that the stitch length is an important parameter for controlling the response of sensor area. By varying this length, response of sensing part may be enhanced in the required specific range.

In exemplary embodiments, an exemplary device (such as device Back to method 200, step 204 may comprise of receiving signals from an end of the conductive part region responsive to receiving electrical signals from the heel region and the ball region. For example, an electrical signal in terms of changing resistance may be generated, when the wearer will walk or run. During a person's physical movement, such as a walk or a ran, they will exert a changing force on the sensing areas, that is, the exemplary ball and heal region. In exemplary embodiments, a wearer may reach faster top speeds not by repositioning their limbs more rapidly in the air, but by applying greater support forces to the ground. Every time, the foot of the wearer touches the ground, it may be counted as one step. Also, every time, the foot of the wearer touches the ground, it will provide a change in resistance depending on the amount of force by which the foot touches the ground. Utilizing values associated with these two parameters, a person's health conditions may be monitored using further calculations.

Step 206 may comprise of utilizing the received signals for determining health of a user. In exemplary embodiments, a different number of plies in the conductive yarn and variation in yarn's structural parameters offers different compression properties and a wider range of change in resistance. The change in resistance of conductive yarn due to pressure applied by the weight of subject wearing socks may be measured using a Wheatstone bridge. Conventional methods of step counting employ GPS-based movements and similar methods. However, the exemplary system provides a more accurate manner of counting steps based on strikes of the heal and ball regions onto the ground resulting in an accurate number of steps.

Since there is a significance variance in the age and height of populations (number of subjects wearing socks), the population may be divided into four main categories based on body mass index (BMI), that is, 19 to 24, 25 to 29, 30 to 39, and 40 to 54. The BMI is an important parameter that indicates when a person has normal weight or is overweight/obesity. BMI of higher than 30 is designated as obesity. Obesity is impacted by metabolic rate, which is the number of calories burned in a unit time. A body consuming and burning equal number of calories in a single day will stay at the same weight. However, for example, if a body burns 500 calories less than it consumes, the weight gain by the body in one week would be 5 kg. The exemplary socks will aid in monitoring the weight loss/gain by continuous monitoring of burring of calories.

In exemplary embodiments, a first step may include obtaining calibrated curves for change in resistance ($\Delta R$) vs. pressure applied (P) by a potential subject wearing socks for reference sensor signals in smart socks. In exemplary embodiments, the heal and ball regions of socks, knitted by conductive yarns with plain, rib and PQ structures collectively serve as a sensor. When a person wearing the exemplary socks, walks, runs, or otherwise exerts pressure on knitted structures made of conductive yarns, a change in resistance ($\Delta R$) may be observed due to applied pressure, which may be utilized to find the applied pressure (P) from calibrated curves. The effective mass (m) of the subject wearing socks may be calculated using Equation 1.

$$m = (P \times A)/g \tag{1}$$

Where 'g' is gravitational acceleration and 'A' is an effective area. In exemplary embodiments, as may be deduced from Equation 1, the effective mass of wearer depends on the pressure applied, effective area, and gravitational force. Each time, an exemplary wearer exerts pressure on the sensing area, the force may be calculated by multiplying pressure into sensing area. Furthermore, mass (m) may be calculated by dividing the force by gravitation force.

In exemplary embodiments, an output of the sensor may be transferred to processing unit. Specifically, the signals generated at exemplary sensing areas may be transferred via conducting paths. The processing unit contains an exemplary processor, Wheatstone bridge, filters, and other communication resources. The processing unit may either be directly attached to conducting paths or it may be connected wirelessly. In exemplary embodiments, processing unit X may count a number of steps, by counting the number of events, the pressure is applied. Considering the stride length of a healthy person of around 0.65 meters, number of miles may be calculated by multiplying stride length with number of steps (1 miles equals to 1609.34 meters). In embodiments, the stride length of population for different age group may also be considered for calculation. If the body mass (m) and distance covered in miles (d) is known, the calories burned during activity (walking and running) may be calculated utilizing equations 2-4 provided below. In exemplary embodiment, calories are continuously burnt, even without any exertion, due to basal metabolism. So, the calories burned during walking or running should be 'net calories burned', which excludes the calories burned due to basal metabolism. A person travelling with a speed of 5 km per hour is supposed to be walking, whereas the speed of 8 km per hour is designated as running.

$$\text{Net Calories burned(Walking)} = 0.30 m \cdot d \quad (2)$$

$$\text{Total Calories burned(Walking)} = 0.53 m \cdot d \quad (3)$$

$$\text{Net Calories burned(Running)} = 0.63 m \cdot d \quad (4)$$

$$\text{Total Calories burned(Running)} = 0.75 m \cdot d \quad (5)$$

Figure 5:
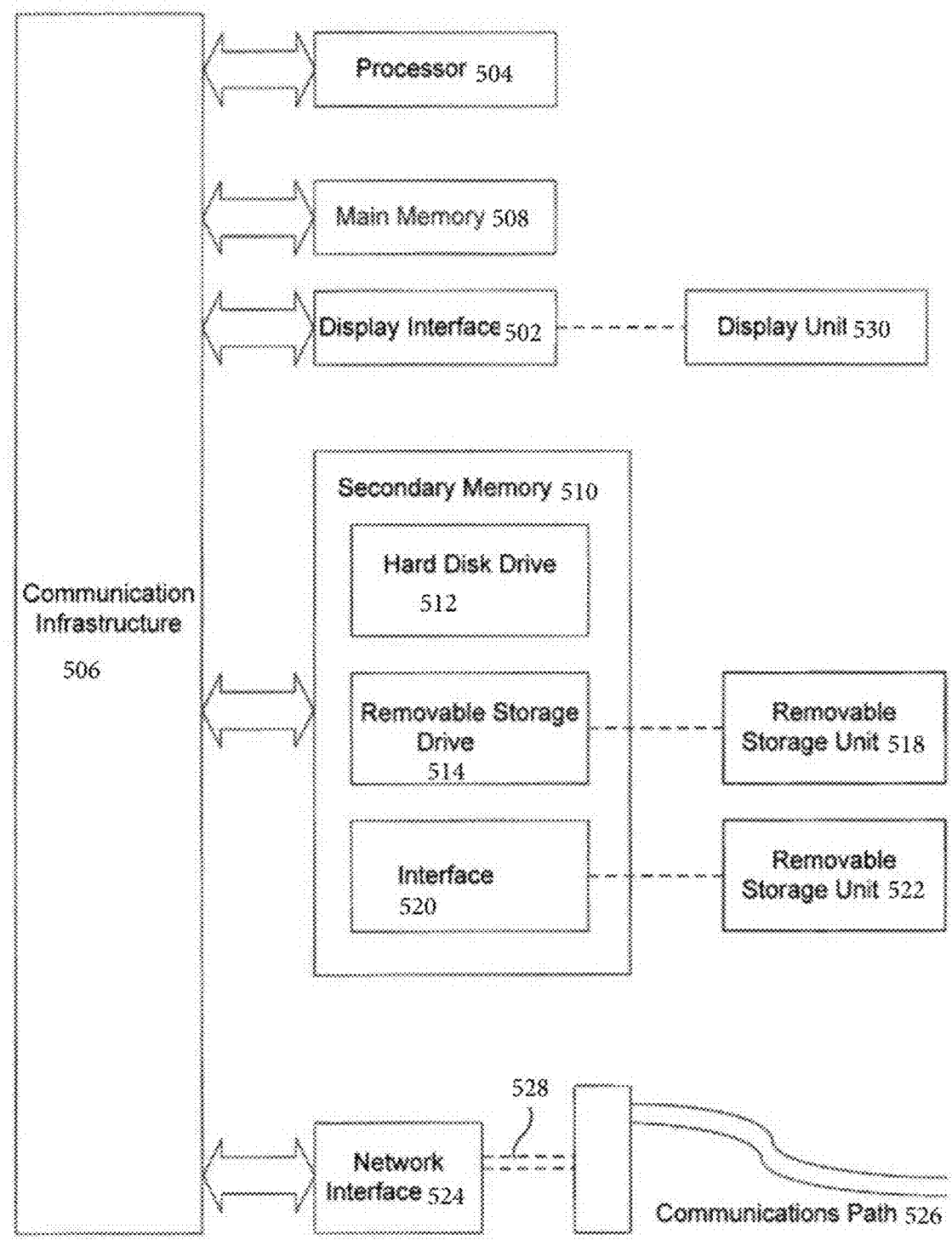
FIG. 5 illustrates an example computer system 500 in which an embodiment of the present invention, or portions thereof, may be implemented as computer-readable code, consistent with one or more exemplary embodiments of the present disclosure.

FIG. 5 illustrates an example computer system/device 500 in which an embodiment of the present invention, or portions thereof, may be implemented as computer-readable code, consistent with exemplary embodiments of the present disclosure. For example, an exemplary device for exemplary steps 204 and 206 may be implemented in computer system 500 using hardware, software, firmware, tangible computer readable media having instructions stored thereon, or a combination thereof and may be implemented in one or more computer systems or other processing systems.

If programmable logic is used, such logic may execute on a commercially available processing platform or a special purpose device. One of ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 504 may be a special purpose or a general-purpose processor device. As will be appreciated by persons skilled in the relevant art, processor device 504 may also be a single processor in a multi-core/multiprocessor system, such system operating alone, or in a cluster of computing devices operating in a cluster or server farm. Processor device 504 is connected to a communication infrastructure 506, for example, a bus, message queue, network, or multi-core message-passing scheme.

Computer system 500 also includes a main memory 508, for example, random access memory (RAM), and may also include a secondary memory 510. Secondary memory 510 may include, for example, a hard disk drive 512, removable storage drive 514. Removable storage drive 514 may comprise a floppy disk drive, a magnetic tape drive, an optical disk drive, a flash memory, or the like. The removable storage drive 514 reads from and/or writes to a removable storage unit 518 in a well-known manner. Removable storage unit 518 may comprise a floppy disk, magnetic tape, optical disk, etc., which is read by and written to by removable storage drive 514. As will be appreciated by persons skilled in the relevant art, removable storage unit 518 includes a computer usable storage medium having stored therein computer software and/or data.

In alternative implementations, secondary memory 510 may include other similar means for allowing computer programs or other instructions to be loaded into computer system 500. Such means may include, for example, a removable storage unit 522 and an interface 520. Examples of such means may include a program cartridge and cartridge interface (such as that found in video game devices), a removable memory chip (such as an EPROM, or PROM) and associated socket, and other removable storage units 522 and interfaces 520 which allow software and data to be transferred from the removable storage unit 522 to computer system 600.

Computer system 500 may also include a communications interface 524. Communications interface 524 allows software and data to be transferred between computer system 500 and external devices. Communications interface 524 may include a modem, a network interface (such as an Ethernet card), a communications port, a PCMCIA slot and card, or the like. Software and data transferred via communications interface 524 may be in the form of signals, which may be electronic, electromagnetic, optical, or other signals capable of being received by communications interface 524. These signals may be provided to communications interface 524 via a communications path 526. Communications path 526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 518, removable storage unit 522, and a hard disk installed in hard disk drive 512. Computer program medium and computer usable medium may also refer to memories, such as main memory 508 and secondary memory 510, which may be memory semiconductors (e.g. DRAMs, etc.).

Computer programs (also called computer control logic) are stored in main memory 808 and/or secondary memory 510. Computer programs may also be received via communications interface 524. Such computer programs, when executed, enable computer system 500 to implement the present invention as discussed herein. In particular, the computer programs, when executed, enable processor device 504 to implement the processes of the present invention, such as the operations in the method illustrated by flowchart 300 of FIG. 3 and flowchart 400 of FIG. 4 discussed above. Accordingly, such computer programs represent controllers of the computer system 500. Where the invention is implemented using software, the software may be stored in a computer program product and loaded into computer system 500 using removable storage drive 514, interface 520, and hard disk drive 512, or communications interface 524.

Embodiments of the invention also may be directed to computer program products comprising software stored on any computer useable medium. Such software, when executed in one or more data processing device, causes a data processing device(s) to operate as described herein. An embodiment of the invention employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Moreover, the word "substantially" when used with an adjective or adverb is intended to enhance the scope of the particular characteristic; e.g., substantially planar is intended to mean planar, nearly planar and/or exhibiting characteristics associated with a planar element. Further use of relative terms such as "vertical", "horizontal", "up", "down", and "side-to-side" are used in a relative sense to the normal orientation of the apparatus.

What is claimed:

1. A manufacturing method of a sock, comprising the steps of:
   a. manufacturing a sock, comprising:
      determining regions for conductive yarn patches in a sock, wherein the regions comprise of a heel region and a ball region;
      determining conductive part regions for a plurality of conductive paths connecting the respective heel region and the respective ball region to a top part of the sock, wherein at least two of the plurality of conductive paths are connected to the ball region and at least two of the plurality of conductive paths are connected to the heal region; and
      stitching the sock comprising stitching utilizing conductive yarn for the conductive yarn patches and the conductive paths utilizing a first stitch length for conductive yarn for the conductive yarn patches and the conductive paths, and stitching utilizing cotton yarn for the remaining of the socks utilizing a second stitch length for cotton yarn for the remaining of the socks, wherein the conductive yarn patches have a width between 4 to 5 cm and a length between 3.5 cm to 5 cm;
   b. receiving signals from an end of the conductive part region responsive to receiving electrical signals from the heel region and the ball region;
   c. utilizing the received signals for determining health of a user.

2. The method of claim 1, wherein the conductive yarn patches consist of only the conductive yarn.

* * * * *